United States Patent
Tanikawa et al.

(10) Patent No.: US 9,017,309 B2
(45) Date of Patent: Apr. 28, 2015

(54) THROMBUS-ASPIRATION CATHETER

(75) Inventors: Masahiro Tanikawa, Osaka (JP); Ryota Umegaki, Osaka (JP); Yuki Nishimura, Osaka (JP)

(73) Assignee: Nipro Corporation, Osaka-shi (JP)

( * ) Notice: Subject to any disclaimer, the term of this patent is extended or adjusted under 35 U.S.C. 154(b) by 720 days.

(21) Appl. No.: 12/594,539

(22) PCT Filed: Apr. 1, 2008

(86) PCT No.: PCT/JP2008/056470
§ 371 (c)(1),
(2), (4) Date: Oct. 2, 2009

(87) PCT Pub. No.: WO2008/123521
PCT Pub. Date: Oct. 16, 2008

(65) Prior Publication Data
US 2010/0049147 A1  Feb. 25, 2010

(30) Foreign Application Priority Data
Apr. 3, 2007 (JP) ................................. 2007-097754

(51) Int. Cl.
*A61M 25/00* (2006.01)
*A61B 17/22* (2006.01)
(Continued)

(52) U.S. Cl.
CPC ............ *A61M 25/0068* (2013.01); *A61B 17/22* (2013.01); *A61B 17/3207* (2013.01); *A61B 2017/22001* (2013.01);
(Continued)

(58) Field of Classification Search
CPC ............... A61B 2217/005; A61B 2017/22079; A61B 2017/22038; A61B 2018/00291; A61M 25/0032; A61M 1/008; A61M 2025/109; A61M 2205/7545; A61M 25/008; A61M 25/0012; A61M 2025/0008; A61M 25/09; A61M 1/0031
USPC .......... 604/265, 525, 43, 272, 508, 93.01, 35, 604/319, 103.1, 529, 533, 523, 164.02, 534, 604/103.04, 528, 530
See application file for complete search history.

(56) References Cited

U.S. PATENT DOCUMENTS 4,995,865 A * 2/1991 Gahara et al. ................... 604/43
5,084,013 A * 1/1992 Takase ............................ 604/43
(Continued)

FOREIGN PATENT DOCUMENTS

JP   64-58263 A    3/1989
JP   11-507251 A   6/1999
(Continued)

*Primary Examiner* — Bhisma Mehta
*Assistant Examiner* — Brandy S Lee
(74) *Attorney, Agent, or Firm* — Birch, Stewart, Kolasch & Birch, LLP

(57) ABSTRACT

It is intended to provide a thrombus-aspiration catheter capable of exerting flexibility and aspiration force even in the case where the tube in the front end side is a triple lumen tube or a contrast marker is provided at the front end. A thrombus-aspiration catheter (1) comprising a basal end side tube (2) of the double lumen type which has an aspiration lumen (11) and a core wire lumen (12), and a front end side tube (3) of the triple lumen type which has a guide wire lumen (13) in addition to the aspiration lumen (11) and the core wire lumen (12), wherein the front end of the above-described front end side tube is obliquely cut and a terminal aspiration tube (4) of a flexible double lumen, which has a front end opening (41) inclined in almost the same direction as the cut face (31), is connected to the cut face.

9 Claims, 4 Drawing Sheets

(51) Int. Cl.
*A61M 25/01* (2006.01)
*A61B 17/3207* (2006.01)

(52) U.S. Cl.
CPC *A61B 2017/22039* (2013.01); *A61B 2217/005* (2013.01); *A61M 25/0029* (2013.01); *A61M 25/0032* (2013.01); *A61M 25/0054* (2013.01); *A61M 25/008* (2013.01); *A61M 25/0108* (2013.01); *A61M 2025/0034* (2013.01); *A61M 2025/0183* (2013.01)

(56) References Cited

U.S. PATENT DOCUMENTS

| | | | |
|---|---|---|---|
| 5,304,140 A | | 4/1994 | Kugo et al. |
| 5,569,215 A | * | 10/1996 | Crocker ................. 604/264 |
| 5,980,505 A | * | 11/1999 | Wilson .................. 604/525 |
| 6,021,340 A | | 2/2000 | Randolph et al. |
| 2003/0120208 A1 | * | 6/2003 | Houser et al. ........ 604/103.04 |
| 2005/0015073 A1 | * | 1/2005 | Kataishi et al. .......... 604/528 |
| 2006/0276774 A1 | * | 12/2006 | Mori ..................... 604/540 |
| 2007/0060911 A1 | * | 3/2007 | Webster et al. ......... 604/528 |
| 2009/0270800 A1 | * | 10/2009 | Spurchise et al. ...... 604/95.04 |

FOREIGN PATENT DOCUMENTS

| | | |
|---|---|---|
| JP | 2004-222946 A | 8/2004 |
| JP | 2004-350901 A | 12/2004 |
| WO | WO-96/40342 A1 | 12/1996 |
| WO | WO 01/32240 A1 | 5/2001 |
| WO | WO-02/083229 A2 | 10/2002 |

* cited by examiner

FIG.4 PRIOR ART
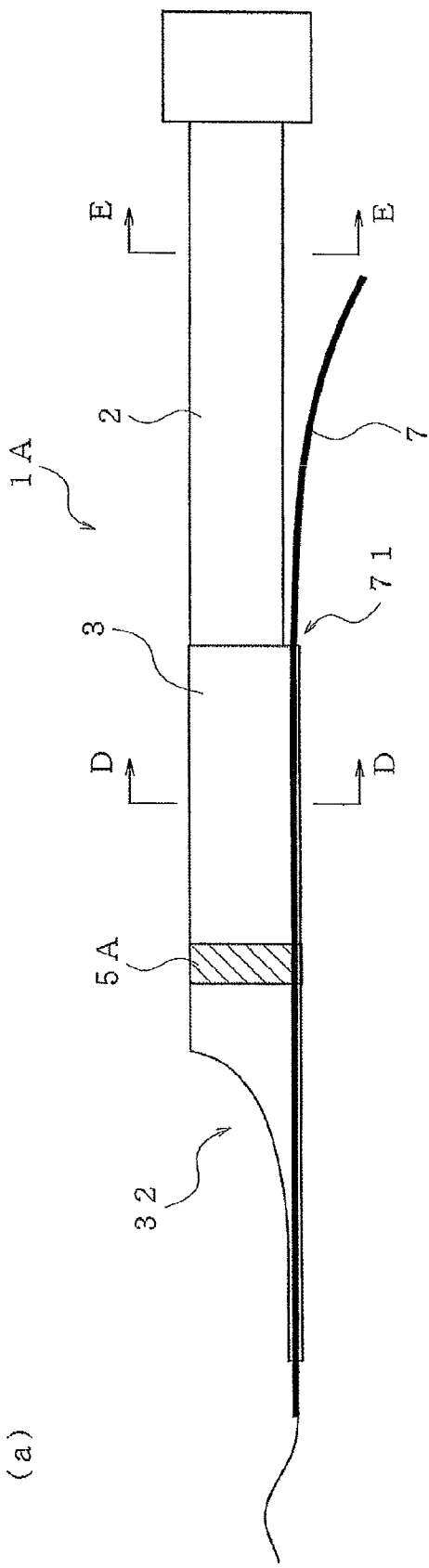
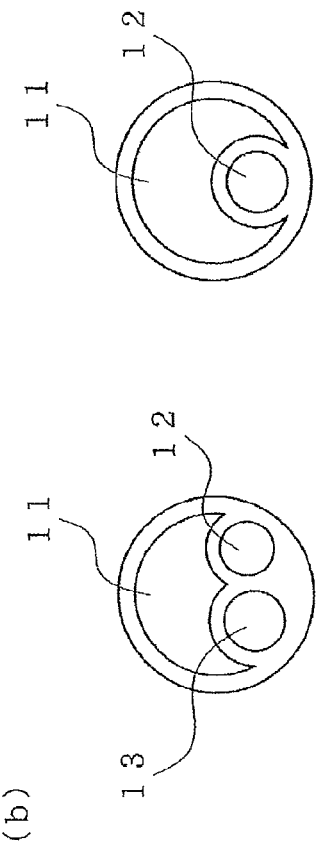

THROMBUS-ASPIRATION CATHETER

TECHNICAL FIELD

The present invention relates to a thrombus-aspiration catheter, and more particularly, it relates to a thrombus-aspiration catheter easily insertable into a curved blood vessel and provided with a high thrombus aspiration property.

BACKGROUND ART

In general, medical practices of injecting a chemical liquid or nutrition into a blood vessel, collecting and testing blood, and dialyzing blood by circulating the blood out of the body are widely carried out through a catheter inserted into/indwelling in the blood vessel.

While a thrombus-aspiration catheter for aspirating a thrombus formed in a cardiac coronary artery is known thereamong, this is a catheter directly aspirating the thrombus growing in the coronary artery in order to prevent such an acute myocardial infarction that the thrombus formed in the coronary blood vessel stops the bloodstream and reduces the cardiac functions.

This thrombus-aspiration cure is a therapy of aspirating and eliminating the thrombus itself by inserting a thin tube of about 1.3 to 2.0 mm in diameter referred to as a thrombus-aspiration catheter from a leg or an arm and making the same reach the lesioned portion in the coronary artery. In the thrombus-aspiration cure, the thrombus, which is the cause constricting the blood vessel, itself is eliminated, whereby risks such as occlusion of the coronary artery with a thrombus not completely dissolvable with a medicine and scattering of the thrombus to coronary artery periphery resulting from dilation with a balloon catheter having been present in a conventional cure can be avoided.

The thrombus-aspiration catheter requires a certain degree of strength so that the wall surface of the catheter is not crushed by negative pressure, and an area (opening area) in an opening section is preferably maximized in order to easily discharge the thrombus from the body.

Thrombus-aspiration catheters include that prepared by inserting a core wire into a tube in order to transmit force for thrusting the catheter necessary for easily inserting the same into a curved blood vessel and to prevent kinks and that prepared by embedding a reinforcing body formed by a metal mesh into a tube. A guide wire is previously inserted into the blood vessel and the thrombus-aspiration catheter is inserted along this guide wire, and hence the front end portion of the thrombus-aspiration catheter is constituted of an aspiration lumen for aspiration and a guide wire lumen for inserting the guide wire.

The front end portion of the catheter is preferably flexible, to be easily inserted into the curved blood vessel.

As a precedent, a thrombus-aspiration catheter improved in aspiration property and cross property by forming a front end opening as an inclined cut surface has already been applied by the applicant (refer to Patent Document 1, for example).

Patent Document 1: Japanese Patent Laying-Open No. 2004-222946

DISCLOSURE OF THE INVENTION

Problems to be Solved by the Invention

In relation to an aspiration catheter employing a triple lumen tube consisting of an aspiration lumen, a guide wire lumen and a core wire lumen as the front end portion of the catheter, however, it has been gradually clarified that flexibility thereof is insufficient when an opening of the front end is merely formed as an inclined cut surface, and a thrombus-aspiration catheter richer in flexibility of the front end portion is awaited.

Further, when an annular contrast marker made of a metal is mounted on the outer side of the tube of the front end portion in order to confirm the position of the front end portion of the thrombus-aspiration catheter in the blood vessel, there arises such a problem that the flexibility of the front end portion is deteriorated.

An object of the present invention is to provide a thrombus-aspiration catheter exhibiting high flexibility of a front end portion and thrombus aspiration force also when a front end-side tube is a triple lumen tube and a contrast marker is provided on the front end portion, in order to solve the aforementioned problems.

Means for Solving the Problems

In order to attain the aforementioned objects, the present invention is characterized in that, in a thrombus-aspiration catheter comprising a basal end-side tube and a front end-side tube connected to the front end side of the basal end-side tube, a terminal aspiration tube is further connected to the front end of the said front end-side tube and the said terminal aspiration tube is more flexible than the said front end-side tube, while the front end side of the said front end-side tube and the basal end side of the said terminal aspiration tube are so connected with each other that the hardness changes stepwise.

According to the present invention having the aforementioned structure, the flexible terminal aspiration tube is connected to the front end of the front end-side tube, whereby the thrombus-aspiration catheter can be improved in flexibility around a front end opening aspirating a thrombus. Further, the aforementioned front end-side tube and the said terminal aspiration tube are so connected with each other that the hardness changes stepwise, whereby a kink resulting from an abrupt hardness change in the connected portion can be prevented.

The present invention is characterized in that the said basal end-side tube is a double lumen tube having an aspiration lumen and a core wire lumen, and the said front end-side tube is a triple lumen tube having a guide wire lumen in addition to an aspiration lumen and a core wire lumen.

According to the present invention having the aforementioned structure, the front end-side tube having the terminal aspiration tube on the front end can be sent to a desired blood vessel position through a guide wire.

The present invention is characterized in that the said terminal aspiration tube is a double lumen tube having an aspiration lumen and a guide wire lumen.

According to the present invention having the aforementioned structure, the terminal aspiration tube can more exhibit flexibility than the front end-side tube of the triple lumen structure, due to the double lumen structure.

The present invention is characterized in that the length of the said terminal aspiration tube is 5 mm to 20 mm. Thus, only a portion around a terminal is flexible.

The present invention is characterized in that the guide wire lumens of the said front end-side tube and the said terminal aspiration tube communicate with each other on the same axis. Thus, the guide wire lumens are straightly linked with each other also on the connected portion.

The present invention is characterized in that both of the materials for the said front end-side tube and the said terminal aspiration tube are prepared from polyamide elastomer, and these are connected with each other by thermal welding.

According to the present invention having the aforementioned structure, the tubes are made of homogeneous resin materials, whereby the same can be reliably thermally welded.

The present invention is characterized in that a front end tip having a guide wire lumen is formed on the front end of the said terminal aspiration tube.

According to the present invention having the aforementioned structure, the small-diametral front end tip having flexibility is so formed on the front end portion of the tube that the catheter can be further easily inserted into a curved blood vessel and a lesioned portion in the blood vessel.

The present invention is characterized in that an aspiration opening is formed by obliquely cutting the front end side of the said terminal aspiration tube.

According to the present invention having the aforementioned structure, the front end side is so obliquely cut that the area of the aspiration opening can be rendered larger than the sectional area of the aspiration lumen while the terminal aspiration tube can be rendered gradually flexible toward the front end.

The present invention is characterized in that a solid contrast marker member is embedded in the tube in the vicinity of the connected portion between the said front end side tube and the terminal aspiration tube.

According to the present invention having the aforementioned structure, the solid contrast marker member is merely inserted into a shaft around the connected portion between the aforementioned front end-side tube and the said terminal aspiration tube, whereby a contrast marker member having a short size and a small diameter can be employed and the flexibility of the front end portion is not deteriorated.

The present invention is characterized in that the outer surfaces of the said front end side tube and the said terminal aspiration tube have lubricative cover layers, whereby frictional resistance in the blood vessel is reduced, and the catheter can more easily reach the lesioned portion.

Effects of the Invention

According to the present invention, the more flexible terminal aspiration tube is connected to the front end of the said front end-side tube in the thrombus-aspiration catheter comprising the basal end-side tube and the front end-side tube, whereby the thrombus-aspiration catheter can be improved in flexibility around the front end opening aspirating a thrombus. Further, the front end-side tube of the triple lumen structure is connected to the flexible aspiration tube of the double lumen structure having the aspiration opening to have a stepwise hardness difference and the solid contrast marker member is embedded in the vicinity of the connected portion, whereby a thrombus-aspiration catheter exhibiting high flexibility and thrombus aspiration force can be obtained also when the front end-side tube is a triple lumen tube and the contrast marker is provided on the front end portion.

BRIEF DESCRIPTION OF THE DRAWINGS

FIG. 4 Shows an exemplary conventional thrombus-aspiration catheter, (a) is a schematic plan view, and (b) shows sectional views in respective portions.

Figure 1:
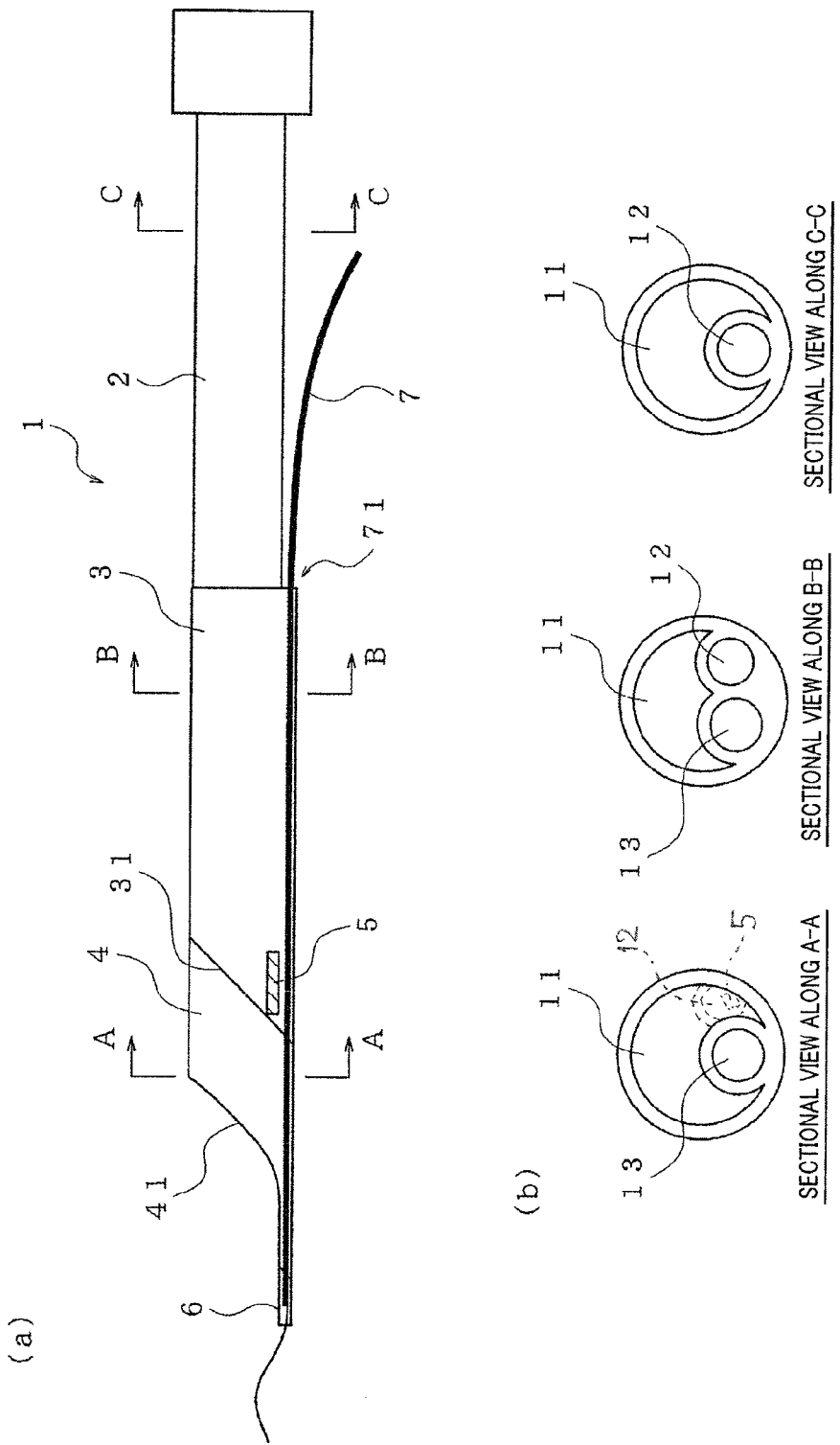
FIG. 1 Shows an exemplary thrombus-aspiration catheter according to the present invention, (a) is a schematic plan view, and (b) shows sectional views in respective portions.

DESCRIPTION OF THE REFERENCE SIGNS 1 thrombus-aspiration catheter
2 basal end-side tube
3 front end-side tube
4 terminal aspiration tube
5 contrast marker member
6 front end tip
7 guide wire
11 aspiration lumen
12 core wire lumen
13 guide wire lumen
31 cut surface
41 aspiration opening

BEST MODES FOR CARRYING OUT THE INVENTION

An embodiment of a thrombus-aspiration catheter according to the present invention is now described in detail with reference to the drawings.

Figure 2:
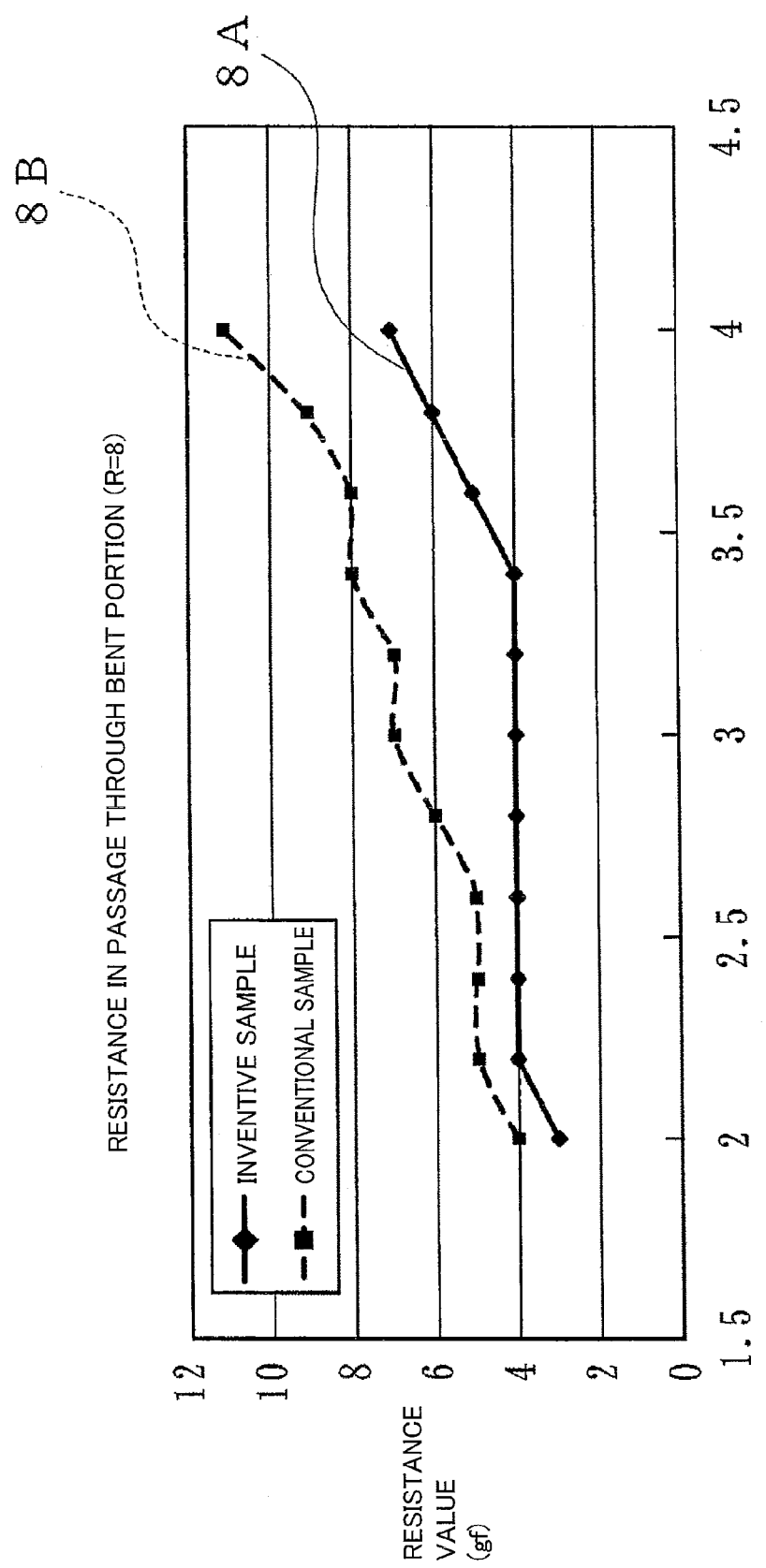
FIG. 2 A line graph showing results obtained by measuring resistance values in passage through a bent portion performed for evaluating flexibility of front end portions.
Figure 3:
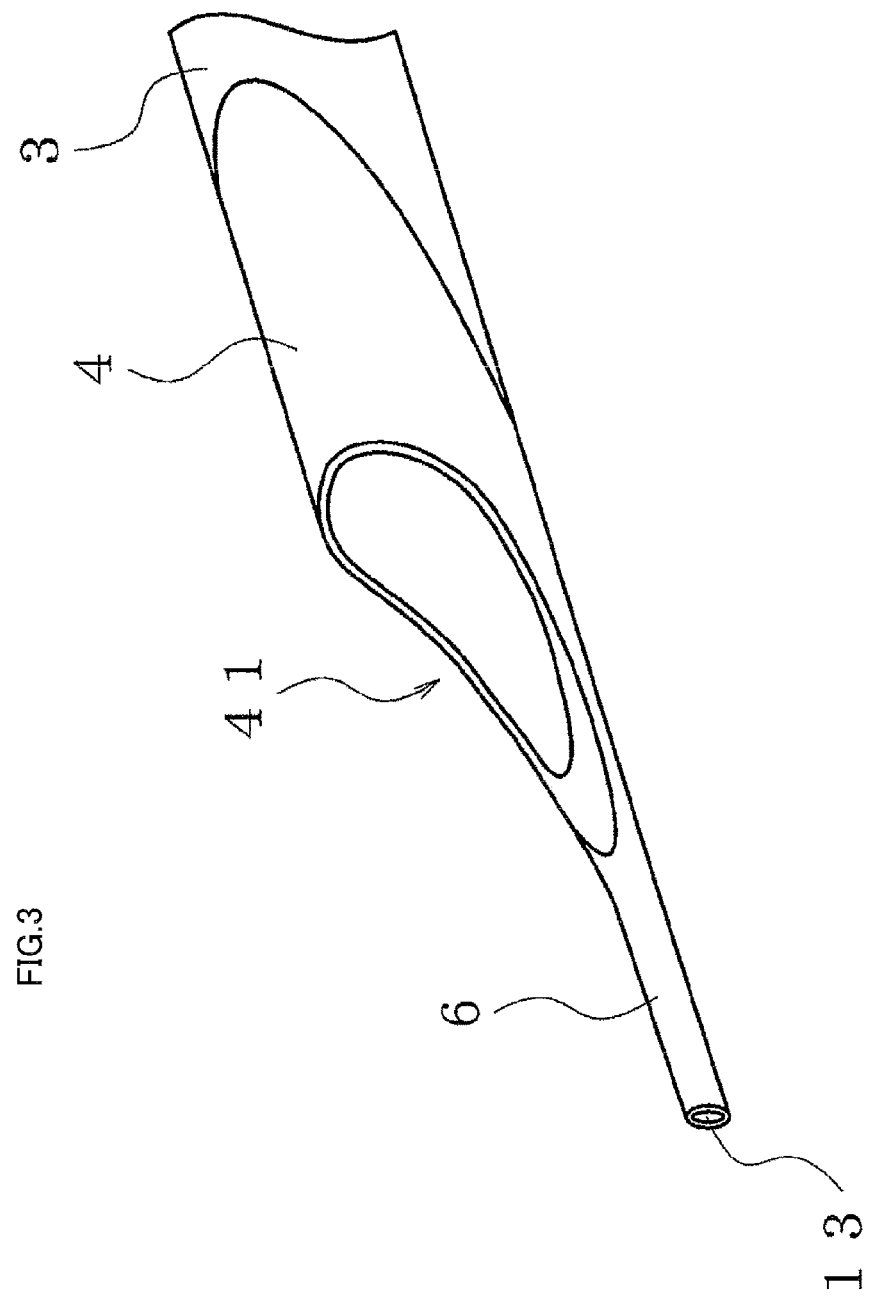
FIG. 3 An enlarged perspective view showing exemplary arrangement of a front end tip according to the present invention.

FIG. 1 shows an exemplary thrombus-aspiration catheter according to the present invention, (a) is a schematic plan view, and (b) shows sectional views in respective portions. FIG. 2 is a line graph showing results obtained by measuring resistance values in passage through a bent portion performed for evaluating flexibility of front end portions. FIG. 3 is an enlarged perspective view showing exemplary arrangement of a front end tip according to the present invention. FIG. 4 shows an exemplary conventional thrombus-aspiration catheter, (a) is a schematic plan view, and (b) shows sectional views in respective portions.

As shown in FIG. 1(a), a thrombus-aspiration catheter 1 according to the present invention comprises a basal end-side tube 2, a front end-side tube 3 and a terminal aspiration tube 4 connected to front end-side tube 3. Terminal aspiration tube 4 is rendered more flexible than said front end-side tube 3, to be easily insertable into a curved blood vessel.

The materials for aforementioned basal end-side tube 2, front end-side tube 3 and terminal aspiration tube 4 can be prepared from thermoplastic resin such as polyethylene, polyamide elastomer, polyester elastomer or polyurethane, for example. In particular, polyamide elastomer (Pebax by Arkema Inc. or the like) allowing selection of various hardness levels in the same material is desirably employed, and Shore hardness levels of the basal end-side tube, the front end-side tube and the terminal aspiration tube are desirably 63D to 72D, 55D to 63D and 40D to 55D respectively.

An aspiration opening 41 aspirating a thrombus or the like is provided in terminal aspiration tube 4. Further, a front end tip 6 is provided on the front end of said terminal aspiration tube 4. In order to render front end tip 6 easily insertable into a desired blood vessel, terminal aspiration tube 4 preferably has a guide wire lumen 13 (see FIG. 3) allowing insertion of a guide wire.

As shown in FIG. 3, terminal aspiration tube 4 connected to front end-side tube 3 is provided with aspiration opening 41 obliquely formed in a large size, becomes gradually flexible toward the front end, and has high thrombus-aspiration performance due to the size of the opening. Further, front end tip 6 formed on the front end has a small diameter, to serve as a pilotage member when the catheter is inserted into the blood vessel. Therefore, thrombus-aspiration catheter 1 comprising front end tip 6 can be preferably easily insertable also into a thin bent blood vessel or a stenosed lesion.

A conventional thrombus-aspiration catheter 1A shown in FIG. 4(*a*) comprises a basal end-side tube 2 and a front end-side tube 3, and an aspiration opening 32 aspirating a thrombus or the like is formed in front end-side tube 3.

Basal end-side tube 2 is a double lumen tube having an aspiration lumen 11 and a core wire lumen 12, as shown in a C-C section of FIG. 1(*b*) and an E-E section of FIG. 4(*b*). Front end-side tube 3 is formed as a triple lumen tube having a guide wire lumen 13 in addition to an aspiration lumen 11 and a core wire lumen 12, as shown in a B-B section of FIG. 1(*b*) and a D-D section of FIG. 4(*b*).

A guide wire 7 can be inserted into guide wire lumen 13 from a guide wire port 71 of front end-side tube 3.

In conventional thrombus-aspiration catheter 1A, an annular contrast marker 5A is mounted on the front end portion. Thus, conventional thrombus-aspiration catheter 1A has such a structure that the front end portion provided with aspiration opening 32 aspirating a thrombus or the like has a triple lumen structure and is mounted with annular contrast marker 5A. In a triple lumen tube, it follows that three chambers are formed in a section thereof, and flexibility is insufficient even if the tube is made of resin which is a flexible material, due to wall portions forming these three chambers. Further, annular contrast marker 5A made of a metal is mounted on the outer side of the tube, and hence flexibility has further been deteriorated.

Thrombus-aspiration catheter 1 according to the present invention has such a structure that the front end of said front end-side tube 3 is obliquely cut to form a cut surface 31 while the basal end side of said terminal aspiration tube 4 is substantially identically cut so that both cut surfaces are connected with each other. Further, terminal aspiration tube 4 is provided with aspiration opening 41 obliquely excised in a large size.

Preferably, terminal aspiration tube 4 is formed as a double lumen tube having an aspiration lumen 11 and a guide wire lumen 13 as shown in an A-A section of FIG. 1(*b*), and the length of the said terminal aspiration tube including the front end tip formed on the front end is 5 mm to 20 mm.

Further, a solid contrast marker member 5 is inserted into the core wire lumen on the obliquely cut front end of said front end-side tube 3, as shown in FIG. 1(*a*).

Said contrast marker member 5 is a short-sized solid round bar of a metal not transmitting X-rays. The material for contrast marker member 5 in the form of a solid round bar can be prepared from platinum, gold, iridium, tungsten, bismuth or an alloy thereof, for example. In particular, the contrast marker member is preferably made of gold, platinum or iridium, in view of a contrast effect by X-ray irradiation.

As hereinabove described, thrombus-aspiration catheter 1 has the structure obtained by embedding the contrast marker member in the form of a solid round bar having a short size and a small diameter in the front end portion of the catheter, whereby flexibility is more improved as compared with the conventional structure obtained by mounting the ring-shaped contrast marker on the outer peripheral portion of the catheter. Further, the contrast marker member is charged into the core wire lumen having a small diameter, whereby local hardness can be suppressed low. In addition, the terminal end portion of the core wire lumen is blocked, whereby there is no possibility that the contrast marker member drops.

Further, solid contrast marker member 5 is inserted into the core wire lumen on the obliquely cut front end of said front end-side tube 3, whereby the flexibility of the obliquely cut front end portion can be improved also in front end-side tube 3 of the triple lumen type relatively inferior in flexibility.

Therefore, passableness into a bent blood vessel is improved without damaging the flexibility of the front end portion of the catheter inserted into an organism, and the catheter easily reaches a lesioned portion. Further, lubricative cover layers are so provided on the outer surfaces of the said front end-side tube and the said terminal aspiration tube that frictional resistance in the blood vessel is reduced and the catheter more easily reaches the lesioned portion.

Results of measurement of resistance values in passage through a bent portion performed for verifying effects of a sample according to the present invention are now described with reference to FIG. 2.

In this experiment, a model prepared by bending a pseudo-blood vessel of resin in a U-shaped manner was employed for measuring and comparing resistance values when actually inserting thrombus-aspiration catheters (thrombus-aspiration catheter 1 according to the present invention and conventional thrombus-aspiration catheter 1A were employed) thereinto. The degree of bending was so set that the bending radius R=8 mm.

More specifically, a guide wire was previously inserted into the aforementioned pseudo-blood vessel model dipped in warm water of 37° C., and resistance values in passage through the bent portion were continuously measured when thrusting a conventional sample and the inventive sample along the guide wire at a constant speed with a load measuring apparatus (Digital Force Gauge DPZ-20N by Imada Seisakusho Co., Ltd.).

Solid line data 8A and broken line data 8B shown in the figure are measurement data of the inventive sample and measurement data of the conventional sample respectively.

While the resistance value of the conventional sample was 4 gf (gram-force) in the initial stage of insertion (upon a lapse of two seconds after the start of the insertion), the resistance value was reduced to about 3 gf in the inventive sample. In the conventional sample, the resistance value was gradually increased from 6 gf to 8 gf, to reach 11 gf in the final stage (upon a lapse of four seconds after the start of the insertion). However, it has been clarified that the inventive sample maintained 4 gf over a relatively long period and was gradually thrust at a constant resistance value. Further, the resistance value was increased merely to about 7 gf in the rearmost portion, and it was possible to obtain a result insertable into the bent portion with a low resistance value.

Passableness through a bent portion is improved as the resistance value in passage through the bent portion is reduced, and hence it is obvious that thrombus-aspiration catheter 1 according to the present invention is superior in flexibility to the conventional sample and improved in passableness through a blood vessel bent portion.

According to the present invention, as hereinabove described, the front end of the front end-side tube having the triple lumen structure and a hand side of the terminal aspiration tube having the double lumen structure are obliquely connected with each other while the flexible terminal aspiration tube of the double lumen structure having the front end opening inclined in the same direction as these connected surfaces is connected, whereby a thrombus-aspiration catheter exhibiting flexibility and aspiration force can be obtained.

Further, the solid contrast marker member is inserted into the core wire lumen on the obliquely cut front end of the front end-side tube, whereby a thrombus-aspiration catheter exhibiting higher flexibility and thrombus-aspiration force can be obtained also when the front end-side tube is a triple lumen tube and the contrast marker is provided on the front end portion.

In addition, the lubricative covering layers are provided on the outer surfaces of the said front end-side tube and the said terminal aspiration tube, whereby a thrombus-aspiration catheter reduced in frictional resistance in a blood vessel to easily reach a lesioned portion can be obtained.

The invention claimed is:

1. A thrombus-aspiration catheter comprising:
a basal end-side tube;
a front end-side tube connected to a front end side of the basal end-side tube;
a terminal aspiration tube connected to a front end of said front end-side tube,
wherein said terminal aspiration tube is more flexible than said front end-side tube, while the front end side of said front end-side tube and a basal end side of said terminal aspiration tube are so connected with each other that a hardness changes stepwisely, and
wherein a front end of said front end-side tube and a basal end side of said terminal aspiration tube have complementary-shaped end surfaces so that both end surfaces are connected with each other, and at least part of the front end of said front end-side tube overlaps with at least part of the basal end side of said terminal aspiration tube in a direction orthogonal to a longitudinal direction of the thrombus-aspiration catheter; and
a solid contrast marker member,
wherein said terminal aspiration tube is a double lumen tube having an aspiration lumen and a guide wire lumen, said front end-side tube is a triple lumen tube having a guide wire lumen, an aspiration lumen and a core wire lumen, and said solid contrast marker member is inserted into the core wire lumen of the front end-side tube on the front end of the front end-side tube.

2. The thrombus-aspiration catheter according to claim 1, wherein said basal end-side tube is a double lumen tube having an aspiration lumen and a core wire lumen.

3. The thrombus-aspiration catheter according to claim 1, wherein said terminal aspiration tube has a length of 5 mm to 20 mm.

4. The thrombus-aspiration catheter according to claim 1, wherein the guide wire lumens of said front end-side tube and said terminal aspiration tube communicate with each other on the same axis.

5. The thrombus-aspiration catheter according to claim 1, wherein both a material for said front end-side tube and a material for said terminal aspiration tube are prepared from polyamide elastomer, and these are connected with each other by thermal welding.

6. The thrombus-aspiration catheter according to claim 1, wherein a front end tip of the guidewire lumen of the terminal aspiration tube is formed on a front end of the terminal aspiration tube.

7. The thrombus-aspiration catheter according to claim 1, wherein an aspiration opening is formed by obliquely cutting a front end side of said terminal aspiration tube.

8. The thrombus-aspiration catheter according to claim 1, wherein a solid contrast marker member is embedded in a vicinity of a connected portion between said front end-side tube and said terminal aspiration tube.

9. The thrombus-aspiration catheter according to claim 1, wherein an outer surface of said front end side tube and an outer surface of the terminal aspiration tube have lubricative cover layers.

* * * * *